(12) United States Patent
Ollivier (10) Patent No.: US 11,357,996 B2
(45) Date of Patent: *Jun. 14, 2022

(54) SYSTEM AND METHOD FOR EXTRA CARDIAC DEFIBRILLATION

(71) Applicant: SORIN CRM SAS, Clamart (FR)

(72) Inventor: Jean-Francois Ollivier, Gif sur Yvette (FR)

(73) Assignee: Sorin CRM SAS, Clamart (FR)

( * ) Notice: Subject to any disclaimer, the term of this patent is extended or adjusted under 35 U.S.C. 154(b) by 61 days.

This patent is subject to a terminal disclaimer.

(21) Appl. No.: 16/908,352

(22) Filed: Jun. 22, 2020

(65) Prior Publication Data

US 2020/0384277 A1 Dec. 10, 2020

Related U.S. Application Data

(63) Continuation of application No. 15/838,058, filed on Dec. 11, 2017, now Pat. No. 10,688,308.

(30) Foreign Application Priority Data

Dec. 12, 2016 (EP) .................................... 16306660

(51) Int. Cl.
*A61N 1/39* (2006.01)
*A61N 1/05* (2006.01)

(52) U.S. Cl.
CPC ......... *A61N 1/3968* (2013.01); *A61N 1/0563* (2013.01); *A61N 1/3918* (2013.01); *A61N 1/3956* (2013.01); *A61N 1/0587* (2013.01); *A61N 1/3925* (2013.01)

(58) Field of Classification Search
None
See application file for complete search history.

(56) References Cited

U.S. PATENT DOCUMENTS

| | | | |
|---|---|---|---|
| 5,235,978 A | 8/1993 | Hirschberg et al. |
| 5,374,279 A | 12/1994 | Duffin et al. |
| 5,849,031 A | 12/1998 | Martinez et al. |
| 6,038,472 A | 3/2000 | Williams et al. |
| 7,715,915 B1 | 5/2010 | Ryu et al. |
| 8,868,213 B2 | 10/2014 | Shan et al. |
| 8,897,879 B2 | 11/2014 | Karamanoglu et al. |
| 2006/0015163 A1 | 1/2006 | Brown |
| 2006/0020316 A1 | 1/2006 | Martinez et al. |
| 2008/0082138 A1 | 4/2008 | Smits |
| 2016/0113586 A1 | 4/2016 | Hemming et al. |

FOREIGN PATENT DOCUMENTS

| | | |
|---|---|---|
| EP | 0 601 338 A1 | 6/1994 |
| EP | 1 557 194 B1 | 10/2008 |

OTHER PUBLICATIONS

International Search Report and Written Opinion dated May 4, 2018. 10 pages.

*Primary Examiner* — Brian T Gedeon
(74) *Attorney, Agent, or Firm* — Foley & Lardner LLP (57) ABSTRACT

A system and method for extra cardiac defibrillation is disclosed. In a particular embodiment, an extra cardiac implantable cardioverter defibrillator system includes an implantable defibrillator having a metal case and a defibrillation lead. The defibrillation lead has a connector at its proximal end for coupling to the implantable defibrillator and a first defibrillation coil electrode at a distal portion of the lead. The first defibrillation electrode configured to be disposed in an inferior vena cava.

20 Claims, 11 Drawing Sheets

SYSTEM AND METHOD FOR EXTRA CARDIAC DEFIBRILLATION

CROSS-REFERENCE TO RELATED PATENT APPLICATION

This application is a continuation of U.S. patent application Ser. No. 15/838,058, filed Dec. 11, 2017, which claims the benefit of and priority to European Patent Application No. 16306660.8, filed Dec. 12, 2016, the entire contents of each of which are hereby incorporated by reference.

FIELD OF THE DISCLOSURE

The present disclosure is generally related to a system and method for extra cardiac defibrillation.

BACKGROUND

The high level of failure of endocardial defibrillation leads has pushed the medical device industry to offer a subcutaneous alternative know as Subcutaneous ICD (S-ICD) whose basic idea is to remove the defibrillation leads from the circulatory system and the heart cavities.

However, S-ICD is not free from risk or difficulty. Apart from the surgical risks, clinical studies involving S-ICD have raised new issues and have shown that S-ICD has not reduced the occurrence of known problems associated with standard implantable defibrillators. The technique has nevertheless been accepted by the medical community because it excludes leads from the venous circulatory system, especially the heart chambers. Exclusion from the heart chambers is very appealing to the medical community as the heart is a sensitive area for patient safety and typically the most severe environment for the leads inducing specific risks related to the mechanical stresses applied to the device.

One of the major drawbacks of S-ICD is the energy level required by the new configuration, which is about twice that of the standard implantable defibrillator. Further, implementation of S-ICD requires the design of a new case, leads, electrodes, installation accessories, and training for the practitioner.

SUMMARY

In a particular embodiment, an extra cardiac implantable cardioverter defibrillator system includes an implantable defibrillator having a metal case and a defibrillation lead. The defibrillation lead includes a connector at a proximal end of the defibrillation lead for coupling to the implantable defibrillator and a first defibrillation coil electrode at a distal portion of the lead. The first defibrillation electrode is configured to be disposed in the inferior vena cava.

Other aspects, advantages, and features of the present disclosure will become apparent after review of the entire application, including the following sections: Brief Description of the Drawings, Detailed Description, and the Claims.

DETAILED DESCRIPTION

An Extra Cardiac ICD (EC-ICD) may be used to avoid some of the problems associated with both the traditional implanted defibrillator and the S-ICD while preserving many of their associated benefits. The EC-ICD implementation does not require leads in the heart chambers and thereby avoids or limits certain risks, including those related to the extraction of leads implanted in the one or more cavities of the heart. Extraction of leads may be very problematic, especially when fibrotic tissue has formed around the distal end of the lead at the lead attachment site.

Referring to the defibrillation implementations external to the heart chambers, it is not necessary for the defibrillation electrode to have physical contact with the heart tissue for defibrillation (concept of the shock box). Instead of physical contact by the electrodes, external implementation rely on maintaining a vector through the greater part of the heart muscle to ensure maximum efficiency of the electric field created by the electrodes.

Further, the complexity of the surgical procedure and practitioners' familiarity with the procedure impacts the adoption of a technology and associated therapy, and affects patient safety. The simplest procedure currently practiced by a majority of practitioners is implantation of a simple defibrillator with a single defibrillation lead implanted at the apex of the right ventricle. Maintaining a familiar implantation procedure limits the risk to patients, reduces development costs and facilitates the adoption of the new technology and associated therapy.

Figure 1:
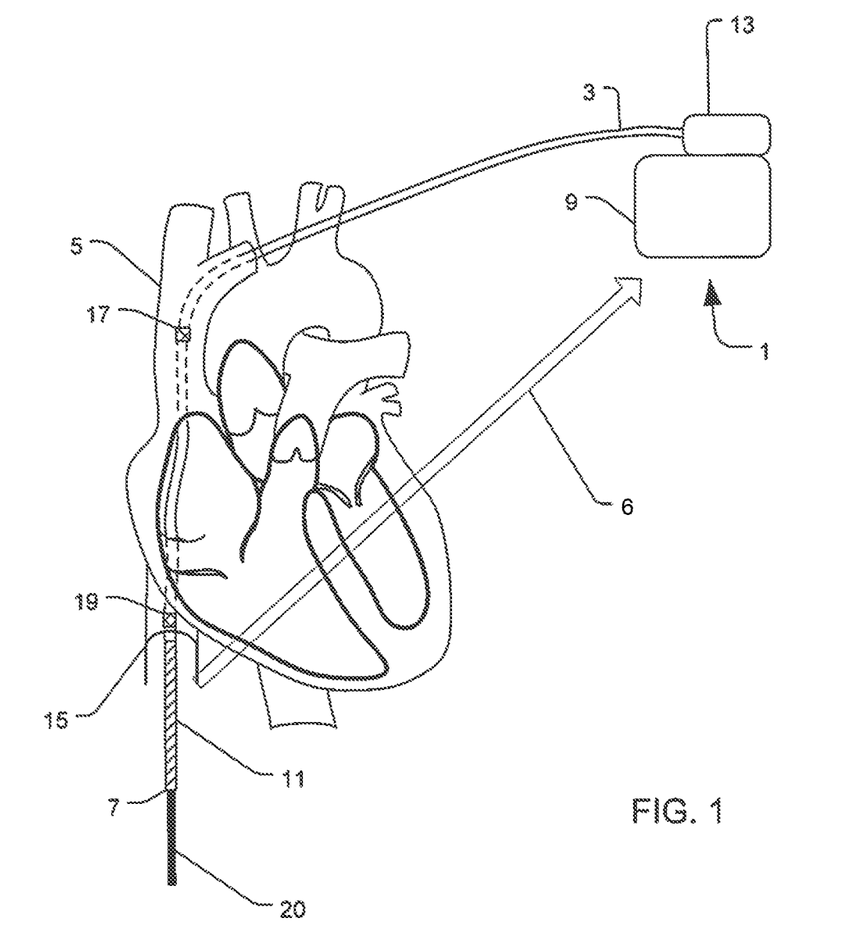
FIG. 1 is a diagram of a particular illustrative embodiment of an Extra Cardiac ICD (EC-ICD)

The EC-ICD implementation provides the benefits of an implantation procedure familiar to the majority of practitioners yet remains outside of the chambers of the heart. Referring to FIG. 1, a particular illustrative embodiment of an EC-ICD is disclosed. The EC-ICD includes an implantable medical device 1, such as an ICD or a CRT-D, and a defibrillation lead 3. The defibrillation lead 3 may be inserted in the body via the classic approach, moving through the superior vena cava (SVC) 5 with the distal end 7 of the lead disposed in the inferior vena cava (IVC) 15. The distal end 7 of the defibrillation lead 3 may include a defibrillation electrode, such as a defibrillation coil electrode. Additional defibrillation electrodes 17 and 19 may be placed along the defibrillation lead. Further, at least a portion of the metal case 9 of the EC-ICD may act as a defibrillation electrode. The distal end 7 of the lead may be left floating in the IVC 15, may be attached to the IVC 15 using a fixation mechanism not electrically connected to the electrode, or a fixation mechanism electrically connected to the electrode.

As illustrated in FIG. 1, the majority of cardiac mass is included within an electric field 6 formed by two electrodes external to the heart chambers, a coil electrode 11 located at the distal end 7 of the lead in the IVC 15 and the case 9 of the EC-ICD. Sensing may also be provided by a dipole formed by at least two of the following components: one or more defibrillation coils, the ICD case, or one or more dedicated sensing electrodes present on the defibrillation lead (e.g., electrodes 17 and 19).

The EC-ICD configuration illustrated in FIG. 1 has no defibrillation electrode (electrically active surface capable of transmitting the high energy) of the implantable device located in the heart chambers but nevertheless use the well-known implantation procedures for implanting the lead into the IVC 15.

The EC-ICD configuration illustrated in FIG. 1 has many advantages over conventional ICD or S-ICD implementations, including implementation simplicity, therapy efficacy, patient safety, and industrial benefits (e.g., reduced cost).

Regarding implementation simplicity, the surgical procedure very close to existing procedures in which the defibrillation lead is implanted via the SVC 5. Further, the EC-ICD configuration, in some embodiments does not even require fixation of the lead to a tissue, thereby further simplifying the implantation procedure.

Regarding therapy efficacy, the EC-ICD of FIG. 1 only requires defibrillation energy at levels similar to the traditional defibrillation approach as opposed to the higher energy levels of S-ICD. For example, longevity of the EC-ICD may be approximately fourteen (14) years compared to seven (7) years for second-generation S-ICDs. A longer lasting device reduces replacement surgeries and the associated risks, including infections. Modifications to the configuration (upgrade) may be easily made without removal of the implanted S-ICD. For example, in sonic embodiments, the device may also provide pacing in one or more of the chambers and/or sensors in one or more of the chambers. In the case of pacing or sensing within the chambers, a separate pacing and/or sensing lead may be provided.

Further, having the defibrillation coil disposed outside of the heart chamber in the IVC reduces the likelihood of damage to the heart tissue surrounding the defibrillation coil compared to traditional intra cardiac ICD implementations cause the electrical field applied to the heart muscle resulting of the remote defibrillation coil is more homogeneous. This remote configuration avoids/limits unnecessary high current density delivered to the tissue surrounding the defibrillation coil. It's commonly acknowledged that the objective of the defibrillation shock is to capture 95% of the heart muscle mass within a minimum electrical field of 5 V/cm not exciding 60 V/cm (permanent damage to the tissue)

Further, the implantation of the EC-ICD of FIG. 1 requires only local anesthesia as opposed to the general anesthesia required for S-ICD implantation, thus reducing hospitalization time of the patient.

Regarding patient safety, the configuration illustrated in FIG. 1 greatly reduces the failure rate of the defibrillation lead. For example, the distal end 7 of the defibrillation lead 3 disposed in the IVC 15 is subject to very little motion which greatly reduces the mechanical failure rate as opposed to a lead attached to the chamber of the heart, which is in constant motion. Further, in some embodiments, a lead design with no attachment mechanism at the distal end 7, such as a retractable mechanism, simplifies the design and reduces the likelihood of mechanical failure. Having no fixation mechanism also reduces issued during implantation and extraction. Further still, the substantial rectilinear trajectory of the lead body improves the ease of implantation and extraction.

Various risks associated with traditional ICD implementations result from lead contact with the heart muscle (interventricular septum or apex). For example, during fixation of a lead, or even during lead extraction, cardiac tamponade may result. Further irreversible damage to portions of the heart muscle may occur during fixation, use of the electrode, and extraction which may further damage the hearts ability to function properly. These risks to the patient are avoided using the EC-ICD implementation illustrated in FIG. 1.

Regarding industrial benefits, the EC-ICD configuration uses components that very similar to those currently used that may require low cost modifications. For example, the development of a defibrillation coil with no fixation mechanism and a metal case 9 that may be used as both a defibrillation electrode and a sensing electrode. Use of this familiar technology with low cost modifications is cheaper and requires less development time than designing a new system for a different environment such as a S-ICD (e.g., requires much higher energy levels and may be affixed the rib cage or other structures outside of the circulatory system).

The case 9 of the EC-ICD system may be set in a very traditional way (e.g., chest position) and may use a very conventional venous access point for entering the circulatory system. A dedicated defibrillation lead 3 may be introduced to the right atrium and then inserted into the inferior vena cava using traditional methods using preshaped stylet or standard 0.014 inch guidewire.

After implantation of the lead 3, the distal end 7 of the lead 3 may include a defibrillation coil defibrillation located in the inferior vena cava. The proximal end of the defibrillation lead may include a standard DF4 connector 13 or other well-known standard connectors.

The lead body may include silicone insulation, a polyurethane tube, or any other well-known bio-compatible insulators. The lead body may include one or more lumens. For example, the lead body may include a multilumen tube. The electrically conductive portions of the lead may include one or more microcables or standard cables located within the lumens, a coil in a central lumen, connection systems microcables to electrodes or coils are classics such as patent description EPI557194B1.

The defibrillation coil 11 may be of standard construction and may include a protective material, such as an insulator, disposed in the gaps between turns of the coil. For example, the protective material may be provided using back filling or BEM. In some embodiments, the coil 11, or exposed portions of the coil (after backfilling or BEM) may be coated with a Carbofilm type of coating. In some embodiments, the entire distal end 7 of the lead 3, a substantial portion of the lead, or the entire lead may be coated with the Carbofilm. The coating may reduce fibrosis formation and limit adhesion to the wall of the IVC of the implanted lead and may facilitate extraction of the lead.

Figure 2:
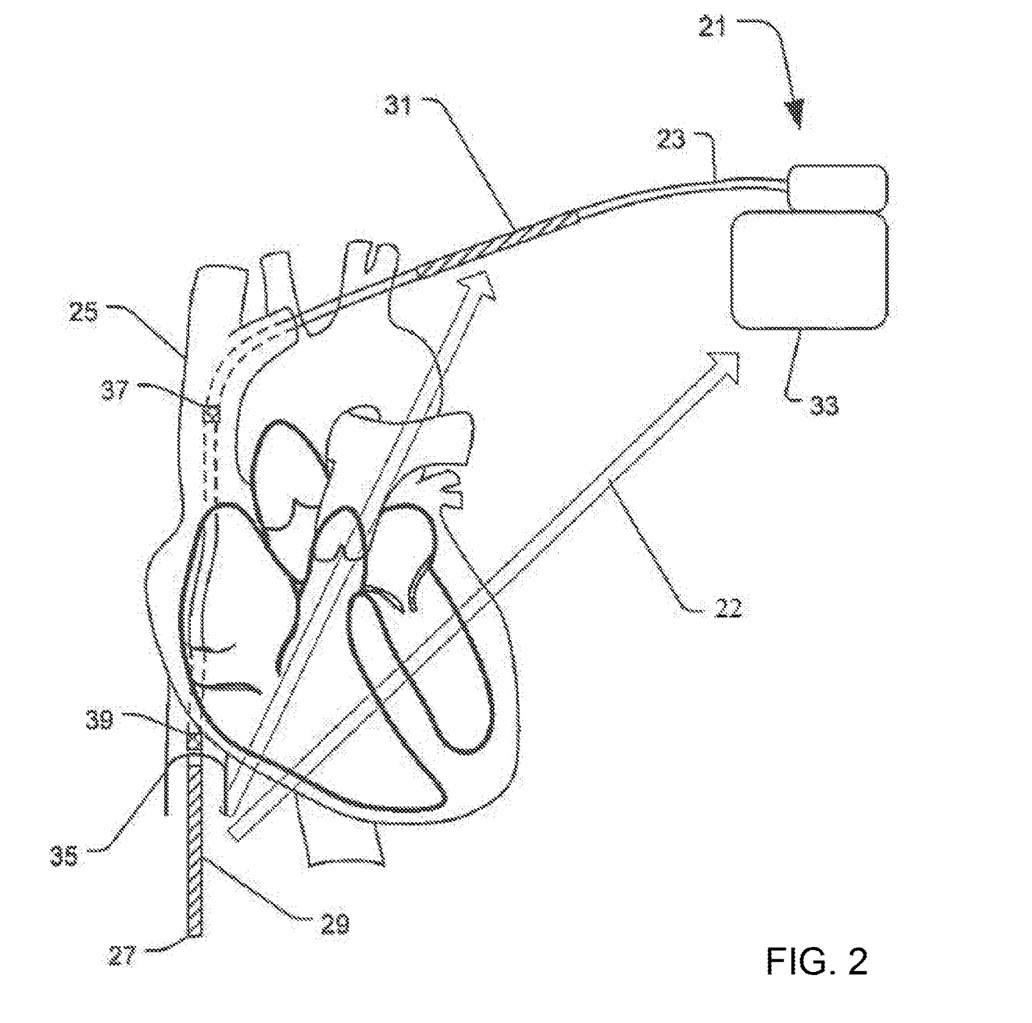
FIG. 2 is a diagram of a particular illustrative embodiment of an EC-ICD.

In some embodiments, a second electrode coil may be positioned between the aforementioned defibrillation coil 11 and the proximal end of the lead. For example, the second electrode coil may be placed between the right atrium and the puncture site in order to offer a wider range of vectors (polarity, orientation) to facilitate defibrillation. In some embodiments, the second electrode coil is located in the SVC as illustrated in FIG. 2

In some embodiments, detection electrodes may be used. Detection electrodes may have a surface area between 5 and 50 mm$^2$. In some embodiments, the detection electrodes may be arranged along the lead body with distances inter-electrode between 2 and 400 mm. A plurality of electrodes may optionally be connected to the same electrical line.

As previously mentioned, in some embodiments, the distal end 7 of the lead 3 is left floating in the IVC 15. To reduce the risk of migration of the floating distal end of the lead, and corresponding defibrillation electrode, into the right atrium or other chambers of the heart, a passive extension 20 (e.g., no electrode) may be added to the distal end of the lead that further extends the distal end of the lead portion already located into the IVC 15. The passive extension 20 may be provided with suitable rigidity to reduce the risk of migration. Having no pacing function, the conceptual risk of micro dislodgement does not exist.

Alternatively, in some embodiments, the practitioner may prefer to affix the distal portion of the lead in the IVC. For example, in some embodiments, it may be desirable to incorporate detection of certain physiological parameters and to improve detection performance it may be preferable to affix or immobilize the lead. To do this several combined solutions are possible. For example, in some embodiments, the distal end of the lead may form a conventional pig tail or hook. In some embodiments, active lateral fixation may be used by screwing the sensing electrode located on the lead body into the IVC or the right atrium. In some embodiments, active distal attachment or passive distal attachment may be used in which the distal end of the lead includes the attachment mechanism, which may be either active (part of the sensing electrode) or passive (electrically isolated from the sensing electrode). In some embodiments, the attachment mechanism may be a stent integral to the lead body or a stent separate from the lead body.

In some embodiments, a DF4 connector 13 may be used to connect the defibrillation electrodes and the detection electrode to the EC-ICD. The standard requires two proximal connections dedicated to the low voltage (typically the sensing function) and the distal connections to the high voltage (defibrillation coil). The central coil (multifilar wires coiled) is typically a low voltage electrical line and traditionally used to connect the most distal pacing electrode leaving a free central lumen for stylet or guidewire insertion during implantation. In some embodiments, to limit change to the conventional design a distal connection is established between the central conductor and a side Microcables. This microcable returns then backward and is adjusted to the desired level of the sensing electrode and connected by conventional means previously cited. The advantage of this arrangement is the maintenance of the standardization of our designs DF4 connector. In some embodiments, microcables housed in the lateral slots of the ML tube(s) coil(s) of the defibrillation or (x) detecting electrodes. The advantage of this arrangement is the maintenance of the standardization of our designs DF4 connector.

In some embodiments, the distal end of the central channel, optionally protected by a seal, may enable the use of a guidewire for placement of the lead. The guidewire may assist the crossing of a valve at the inferior vena cava. This alternative will require a channel end of the diameter adjustment consisting in securing the use of a standard stylet (distal ball of larger diameter than the distal opening of the central lumen)

Table 1 below provides various benefits EC-ICD provides over S-ICD and the standard single chamber ICD defibrillators. The information in Table 1 is not meant to be limiting.

TABLE 1

| Versus S-ICD | Versus standard single chamber ICD |
|---|---|
| Easier implant procedure (shorter duration) remaining in EP hands under standard techniques Expected lifetime 14 years versus 7 years for a smaller device in standard position | Easier implant procedure (shorter duration) cause no pacing threshold to perform, no septal placement . . . Lower risk of less complication related to leads: 2.4 times less of extraction risk than single ICD 3.8 times less of extraction risk than all devices together |
| Easier upgrade to RV pacing (RV pacing lead added from already implanted device) | Lower extraction risk if required (no risk of cardiac perforation) |
| Upgradable to CRT-D (no accessible even with leadless capsule technology for years) | Less deleterious shock (more homogeneous electrical field over the heart) |
| Remain local anesthesia | No device through tricuspid valve (compatibility with mechanical valve Maybe requiring active fixation in IVC) |
| Less painful shocks due to lower energy Only 1 scar (vs 2 or 3 for S-ICD) | No MRI tip temperature elevation issue (no pacing electrode) |

Referring to FIG. 2, a particular illustrative embodiment of an EC-ICD is disclosed. The EC-ICD includes an implantable medical device 21, such as an ICD or a CRT-D, and a defibrillation lead 23. The defibrillation lead 23 may be implanted through the superior vena cava (SVC) 25 with the distal end 27 of the lead 23 disposed in the inferior vena cava (IVC). The distal end 27 of the defibrillation lead may include a defibrillation electrode 29, such as a defibrillation coil electrode. An additional defibrillation electrode 31 is placed along the defibrillation lead 23 in the left brachiocephalic vein (LBCV). Further, at least a portion of the metal case 33 of the EC-ICD may act as a defibrillation electrode. This arrangement provides to the physician more vector options to capture the largest heart mass depending of the relative positions of the coil electrodes, the case and the heart anatomy. In some embodiments, the metal case may be deactivated, as illustrated in FIG. 2. The distal end 27 of the lead 23 may be left floating in the IVC 35, may be attached to the IVC 35 using a fixation mechanism not electrically connected to the electrode, or a fixation mechanism electrically connected to the electrode.

As illustrated in FIG. 2, the majority of cardiac mass is included within an electric field 22 formed by two electrodes 29, 31 external to the heart chambers, a coil electrode 29 located at the distal end of the lead in the IVC 35 and the second coil 31 positioned more proximal on the lead at the LBVC. Sensing may also be provided by a dipole formed by at least two of the following components: one or more defibrillation coils, the ICD case, or one or more dedicated sensing electrodes present on the defibrillation lead (e.g., electrodes 37 and 39).

Figure 3:
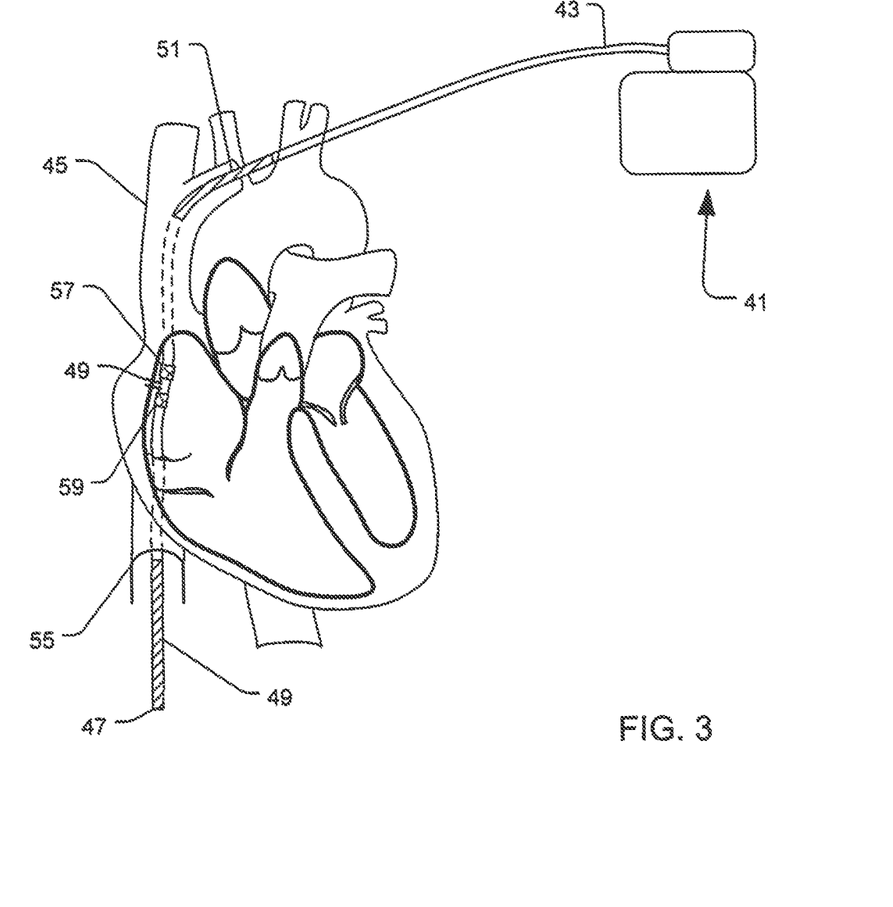
FIG. 3 is a diagram of a particular illustrative embodiment of an EC-ICD.

Referring to FIG. 3, a particular illustrative embodiment of an EC-ICD is disclosed. The EC-ICD includes an implantable medical device 41, such as an [CD or a CRT-D, and a defibrillation lead 43. The defibrillation lead 43 may be implanted through the superior vena cava (SVC) 45 with the distal end 47 of the lead 43 disposed in the inferior vena cava (IVC) 55. The distal end 47 of the defibrillation lead may include a defibrillation electrode, such as a defibrillation coil electrode 49. An additional defibrillation electrode 51 may be placed along the defibrillation lead in the left brachiocephalic vein (LBCV). Further, at least a portion of the metal case of the EC-ICD may act as a defibrillation electrode.

The distal end 47 of the lead 43 may be left floating in the IVC 55 or may be attached to the IVC 55 using a fixation mechanism. In some embodiments, active or passive lateral fixation may be used by screwing the sensing electrode located on the lead body into the IVC or the right atrium. For example, as illustrated in FIG. 3, a fixation mechanism 49 may be provided along the lead body at the right atrium. In some embodiments, the fixation mechanism 49 may be a screw. The fixation mechanism 49 may be active (e.g., serve as a pacing or sensing electrode) or passive. In some embodiments, one or more electrodes may be positioned in the right atrium for sensing and/or pacing (e.g., electrodes 57 and 59). For example, a dipole sensor may be positioned on the lead body in the right atrium.

Figure 4:
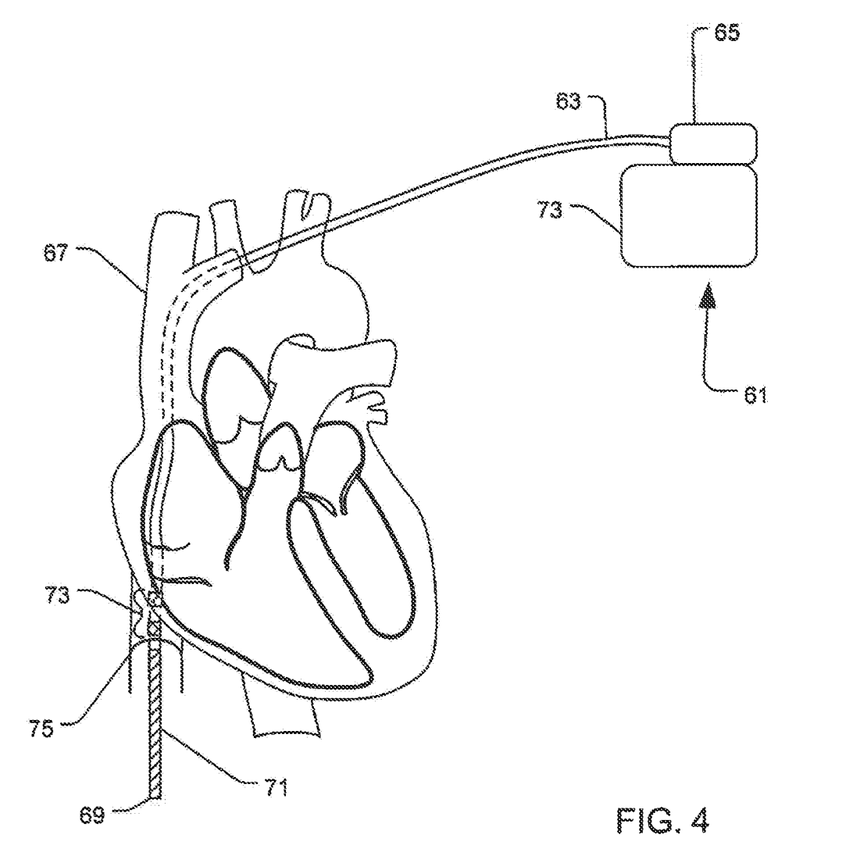
FIG. 4 is a diagram of a particular illustrative embodiment of an EC-ICD.

Referring to FIG. 4, a particular illustrative embodiment of an EC-ICD is disclosed. The EC-ICD includes an implantable medical device 61, such as an ICD or a CRT-D, and a defibrillation lead 63. The connector 65 at the header may be a DF4 connector type. The defibrillation lead 63 may be implanted through the superior vena cava (SVC) 67 with the distal end 69 of the lead 63 disposed in the inferior vena cava (IVC) 75. The distal end 69 of the defibrillation lead may include a defibrillation electrode, such as a defibrillation coil electrode 71. Additional defibrillation electrodes may be placed along the defibrillation lead. Further, at least a portion of the metal case 73 of the EC-ICD may act as a defibrillation electrode and/or a sensing electrode. The distal end 69 of the lead may be left floating in the IVC 75, may be attached to the IVC 75 using a fixation mechanism not electrically connected to the electrode, or a fixation mechanism electrically connected to the electrode. The distal end 69 of the lead may also include at least one electrode. For example, the distal end 69 of the lead 63, just before the defibrillation coil electrode 71 may include a dipole 73 as illustrated in FIG. 4. The dipole 73 may be used to sense and or pace the right ventricle.

Figure 5:
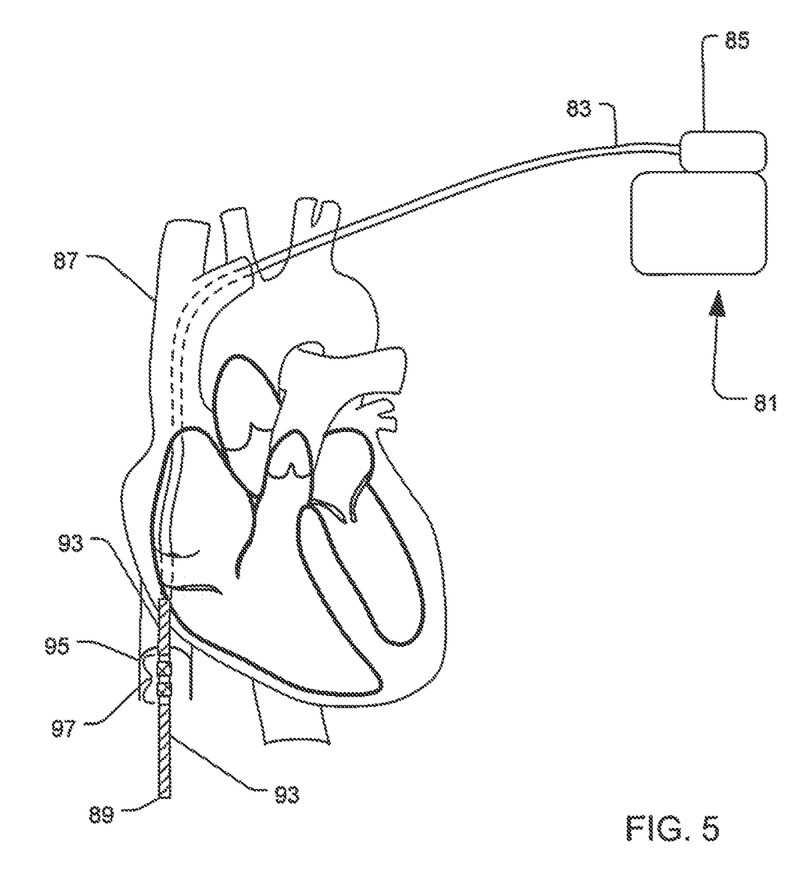
FIG. 5 is a diagram of a particular illustrative embodiment of an EC-ICD.

Referring to FIG. 5, a particular illustrative embodiment of an EC-ICD is disclosed. The EC-ICD includes an implantable medical device 81, such as an ICD or a CRT-D, and a defibrillation lead 83. The connector 85 at the header may be a DF4 connector type. The defibrillation lead 83 may be implanted through the superior vena cava (SVC) 87 with the distal end 89 of the lead 83 disposed in the inferior vena cava (IVC) 95. The distal end 89 of the defibrillation lead may include a defibrillation electrode, such as a defibrillation coil electrode. Additional defibrillation electrodes may be placed along the defibrillation lead. Further, at least a portion of the metal case of the EC-ICD may act as a defibrillation electrode and/or a sensing electrode.

The distal end of the lead may be left floating in the IVC 95, may be attached to the IVC 95 using a fixation mechanism not electrically connected to the electrode, or a fixation mechanism electrically connected to the electrode. In some embodiments, the distal end 89 of the lead 83 may include two electrode coils 91, 93 at the same potential as illustrated in FIG. 5. The distal end of the lead may also include a sensing or high energy pacing (high energy is certainly required due to the distance to the first RV excitable tissue) electrode. For example, a dipole 97 may be positioned between the two electrode coils 91 and 93 to sense or pace at high energy the right ventricle.

Figure 6:
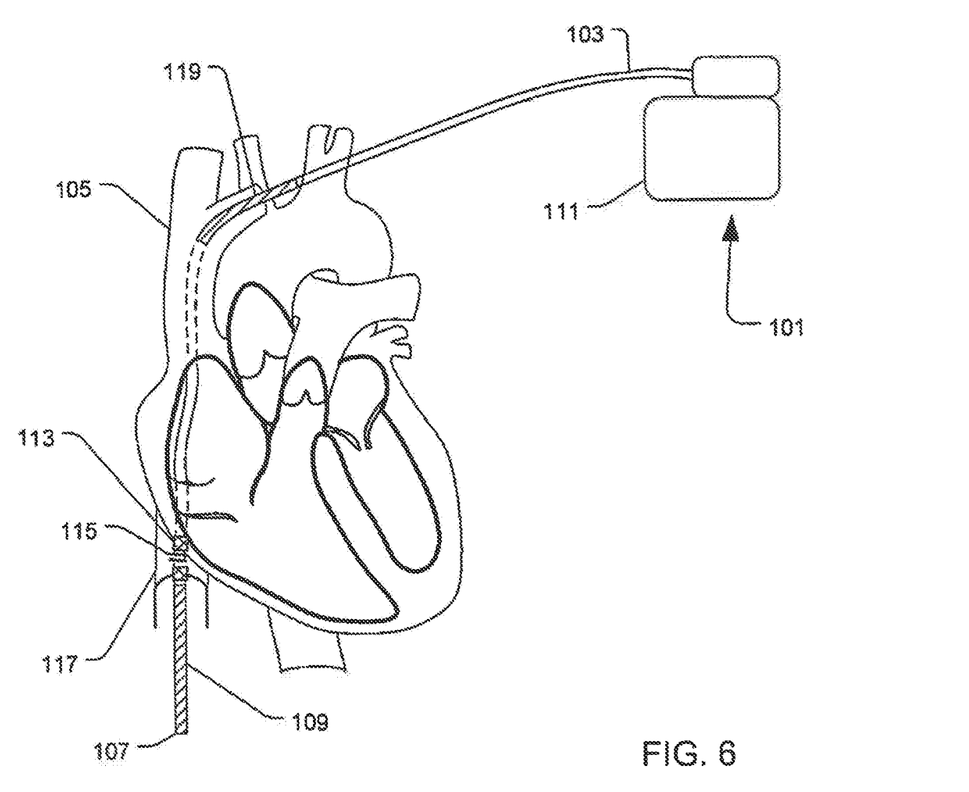
FIG. 6 is a diagram of a particular illustrative embodiment of an EC-ICD.

Referring to FIG. 6, a particular illustrative embodiment of an EC-ICD is disclosed. The EC-ICD includes an implantable medical device 101, such as an ICD or a CRT-D, and a defibrillation lead 103. The defibrillation lead 103 may be implanted through the superior vena cava (SVC) 105 with the distal end 107 of the lead disposed in the inferior vena cava (IVC) 117. The distal end 107 of the defibrillation lead may include a defibrillation electrode 109, such as a defibrillation coil electrode. An additional defibrillation electrode 119 may be placed along the defibrillation lead. Further, at least a portion of the metal case 111 of the EC-ICD may act as a defibrillation electrode and/or a sensing electrode.

The distal end 107 of the lead 103 may be left floating in the IVC 117, may be attached to the IVC 117 using a fixation mechanism not electrically connected to the electrode, or a fixation mechanism electrically connected to the electrode. The distal end 107 of the lead 103 may also include at least one electrode. For example, the distal end of the lead, just before the defibrillation coil electrode 109 may include a dipole 113 as illustrated in FIG. 6. The dipole 113 may be used to pace and or sense the right ventricle. In some embodiments, active or passive fixation may be used to secure the lead body near the distal end to the IVC 117. For example, as illustrated in FIG. 6, a fixation mechanism 115 may be provided near or between the dipoles to secure the lead to the wall of the IVC 117 to improve stability for sensing and or pacing.

Figure 7:
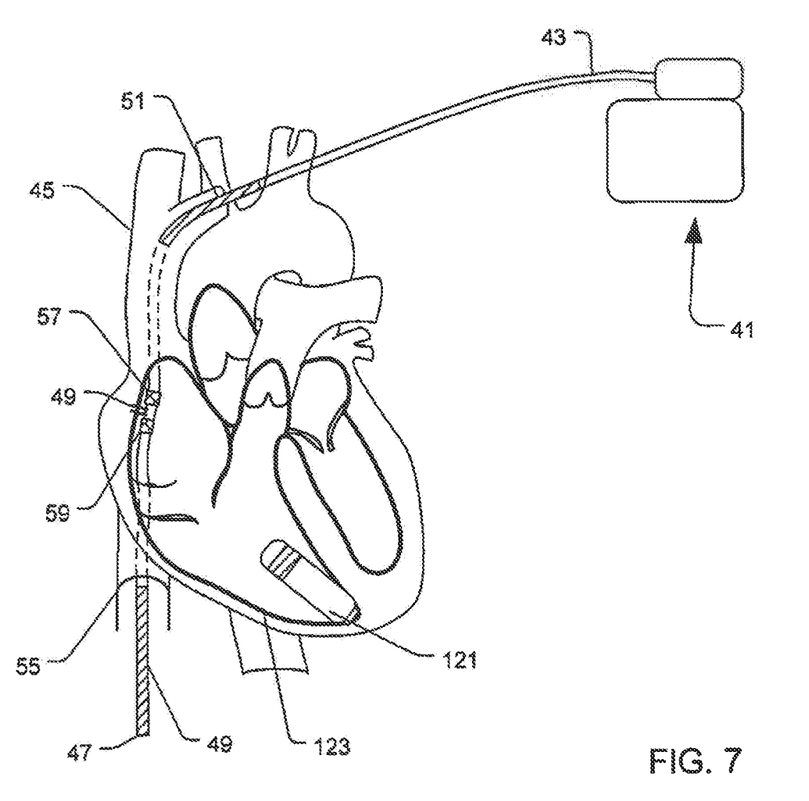
FIG. 7 is a diagram of a particular illustrative embodiment of an EC-ICD.

Referring to FIG. 7, a particular illustrative embodiment of an EC-ICD is disclosed. The EC-ICD configuration may be the same as that of FIG. 3 with the addition of a leadless pacing device 121. One or more leadless pacing devices may be implanted in one or more chambers of the heart to pace the heart. For example, a leadless pacer 121 may be implanted in the right ventricle 123, as illustrated in FIG. 7. The leadless pacer and the EC-ICD may wirelessly communicate data, such as pacing data, sensing data, settings, defibrillation data, or any other kind of physiological or patient data. In some embodiments, the leadless pacer and the EC-ICD operate independently of one another.

Figure 8:
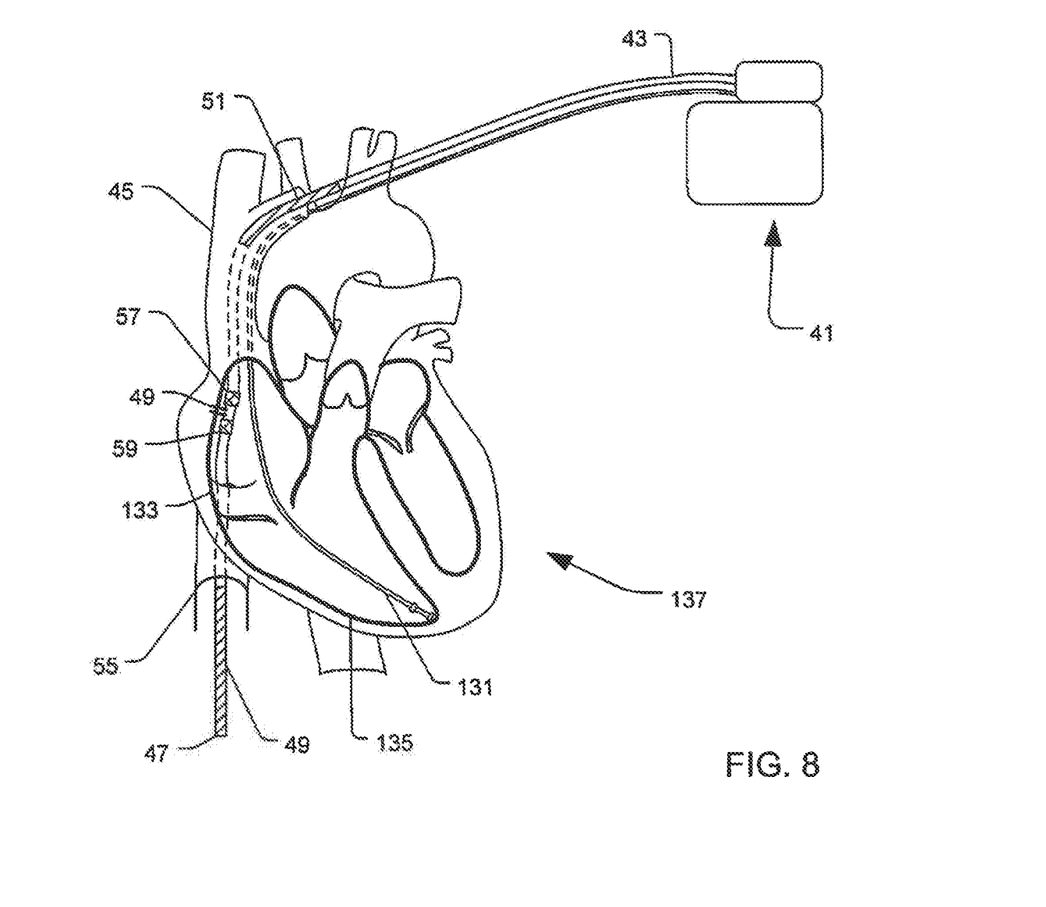
FIG. 8 is a diagram of a particular illustrative embodiment of an EC-ICD.

Referring to FIG. 8, a particular illustrative embodiment of an EC-ICD is disclosed. The EC-ICD configuration may be similar to that of FIG. 3 with the addition of pacing functionality. One or more pacing leads 131 may be connected to the EC-ICD and placed in one or more chambers 133, 135 of the heart 137 to pace the heart 137. For example, a pacing lead 131 may be implanted in the right ventricle, as illustrated in FIG. 8.

Figure 9:
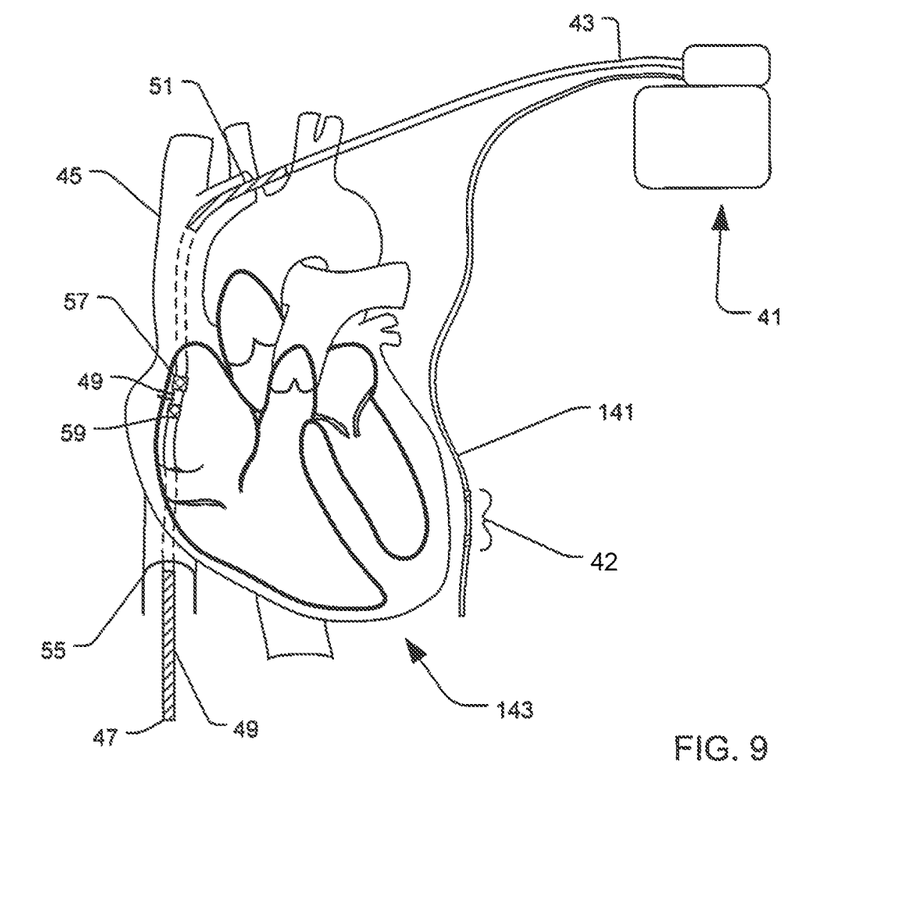
FIG. 9 is a diagram of a particular illustrative embodiment of an EC-ICD.

Referring to FIG. 9, a particular illustrative embodiment of an EC-ICD is disclosed. The EC-ICD configuration may be similar to that of FIG. 3 with the addition of a pacing/sensing lead 141 with one or more pacing/sensing electrodes 42. One or more leads may be connected to the EC-ICD and placed system, but near the heart 143 to pace and or sense heart. For example, a pacing/sensing lead 141 could be located in the left phrenic vein or in the right or left thoraxic vein, as illustrated in FIG. 9.

Figure 10:
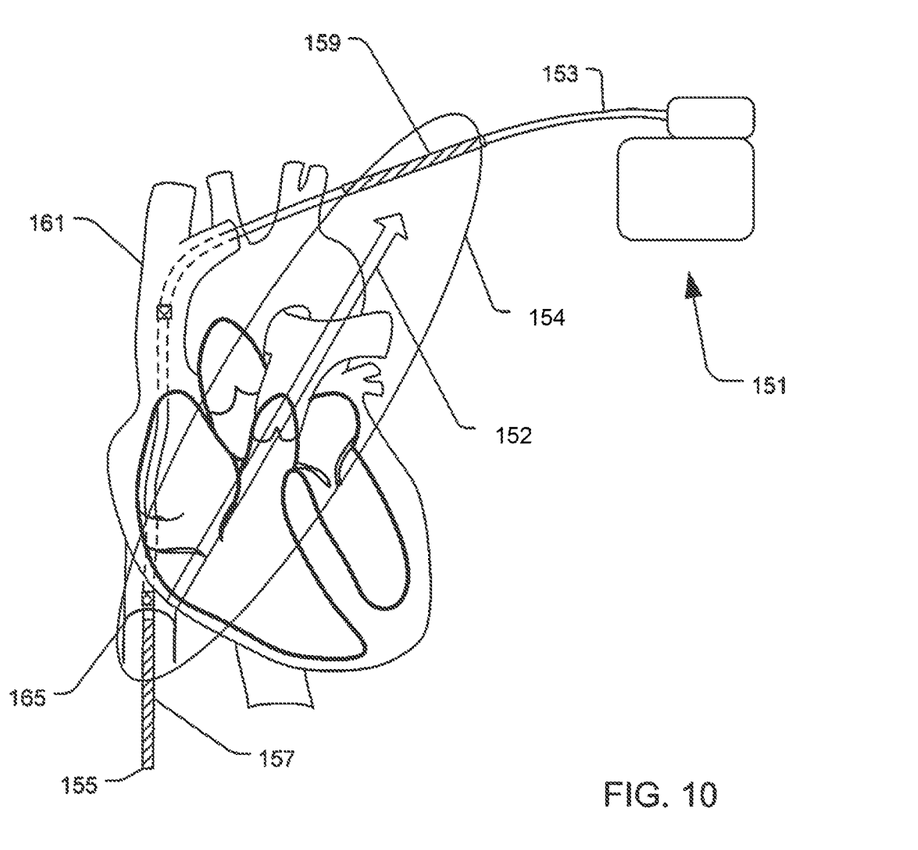
FIG. 10 is a diagram of a particular illustrative embodiment of an EC-ICD.

Referring to FIG. 10, a particular illustrative embodiment of an EC-ICD is disclosed. The EC-ICD configuration may be similar to that of FIG. 2. The EC-ICD includes an implantable medical device 151 and a defibrillation lead 153. The distal end 155 of the defibrillation lead 153 may include a defibrillation coil electrode 157 located at the IVC 165 and a second defibrillation electrode coil 159 placed along the defibrillation lead 153 in the left brachiocephalic vein (LBCV) of the SVC 161. The distal end 155 of the lead may be left floating in the IVC, may be attached to the IVC using a fixation mechanism.

Figure 11:
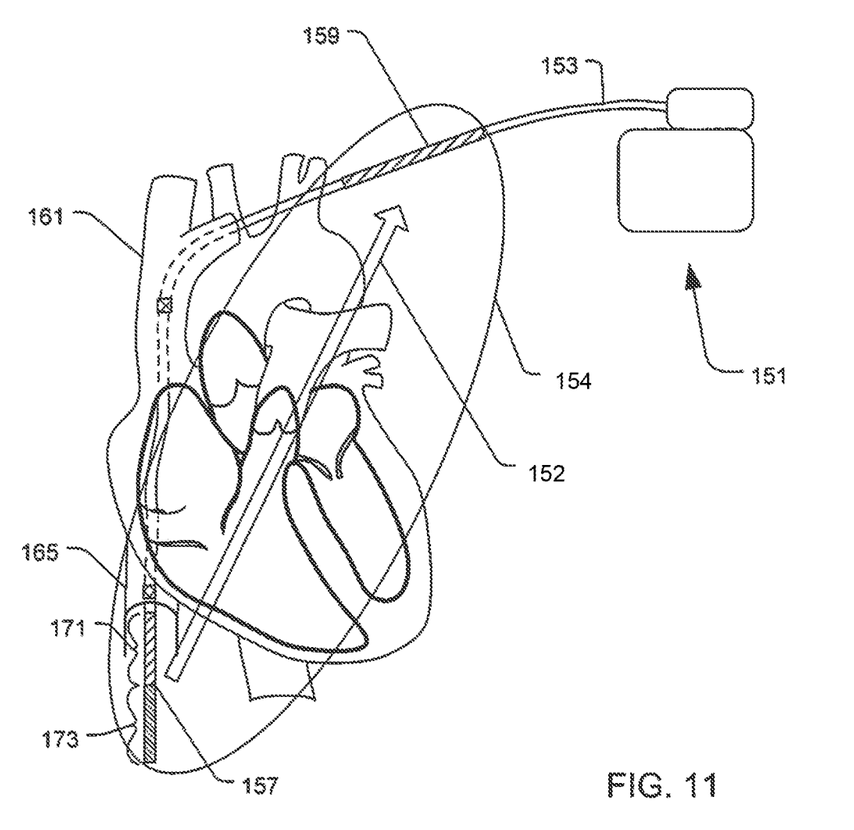
FIG. 11 is a diagram of a particular illustrative embodiment of an EC-ICD.

In some embodiments, it may be beneficial to vary the active area along the distal electrode coil 157 to avoid an electric field concentration 154 surrounding the electric field 152 around the proximal end 159 of the distal electrode coil in the IVC 165, as illustrated in FIG. 10. In some embodiments, the coil surface density may be varied such that a proximal end or portion of the coil 171 has a lower surface density than a distal end or portion 173 as illustrated in FIG. 11.

The presence of one or more defibrillation coils in the circulatory system, but outside the chambers of the heart, such as the IVC, opens the possibility of new vectors for treating atrial fibrillation at low energy (cardioversion) without adversely affecting the right or left ventricular cavities. For example, the vector combination may include IVC→SVC, IVC→RA OD or a combination IVC+SVC-→CAN.

The ICD case in most instances will be implanted at the patient's left side, but if the access veins in that direction were unusable, the case can be positioned right and may be active or not and/or may be used with a single lead having two electrode coils.

Alternatively, in some embodiments, all or part of the defibrillation coil or coils may be positioned in various branches of the vena cava, such as a major veins associated with the IVC, including, the right hepatic vein, middle hepatic vein, or left hepatic vein.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. An extra cardiac implantable cardioverter defibrillator system, comprising:
    an implantable defibrillator having a metal case;
    a defibrillation lead comprising:
        a connector at a proximal end of the defibrillation lead for coupling to the implantable defibrillator; and
        a first defibrillation coil electrode at a distal portion of the lead, the first defibrillation coil electrode configured to be disposed in an inferior vena cava, and wherein the first defibrillation coil electrode has a variable surface density.

2. The extra cardiac implantable cardioverter defibrillator system of claim 1, wherein a proximal portion of the first defibrillation electrode coil has a lower surface density than a distal portion of the first defibrillation electrode coil.

3. The extra cardiac implantable cardioverter defibrillator system of claim 1, wherein at least a portion of the metal case is a defibrillation electrode to form a first defibrillation vector between the first defibrillation coil electrode and the defibrillation electrode of the metal case.

4. The extra cardiac implantable cardioverter defibrillator system of claim 1, wherein the defibrillation lead further comprises a second defibrillation coil electrode proximal to the first defibrillation electrode.

5. The extra cardiac implantable cardioverter defibrillator system of claim 4, wherein the first defibrillation coil electrode and the second defibrillation coil electrode form a defibrillation vector.

6. The extra cardiac implantable cardioverter defibrillator system of claim 5, wherein the defibrillation vector is configured to pass through a heart of a patient when the defibrillation lead is positioned within the patient.

7. The extra cardiac implantable cardioverter defibrillator system of claim 1, wherein the first defibrillation coil electrode has an active area that varies along a length of the first defibrillation coil electrode.

8. The extra cardiac implantable cardioverter defibrillator system of claim 1, wherein the defibrillation lead further comprises at least one electrode proximal to the first defibrillation coil electrode.

9. The extra cardiac implantable cardioverter defibrillator system of claim 8, wherein a sensor of the at least one electrode is configured to be disposed in a right atrium.

10. An extra cardiac implantable cardioverter defibrillator system, comprising:
    an implantable defibrillator;
    a defibrillation lead comprising:
        a connector at a proximal end of the defibrillation lead for coupling to the implantable defibrillator;
        a first defibrillation coil electrode at a distal portion of the lead, the first defibrillation coil electrode configured to be disposed in an inferior vena cava;
        at least one electrode proximal to the first defibrillation coil electrode, wherein one or more of the at least one electrodes and the first defibrillation coil electrode form a dipole; and
        a fixation mechanism disposed between one of the at least one electrodes and the first defibrillation coil electrode.

11. The extra cardiac implantable cardioverter defibrillator system of claim 10, wherein the implantable defibrillator has a metal case.

12. The extra cardiac implantable cardioverter defibrillator system of claim 11, wherein at least a portion of the metal case is a defibrillation electrode to form a first defibrillation vector between the first defibrillation coil electrode and the defibrillation electrode of the metal case.

13. The extra cardiac implantable cardioverter defibrillator system of claim 10, wherein the fixation mechanism is electrically connected to one or more of the at least one electrode.

14. The extra cardiac implantable cardioverter defibrillator system of claim 13, wherein the fixation mechanism is an active fixation mechanism.

15. The extra cardiac implantable cardioverter defibrillator system of claim 10, wherein the fixation mechanism is not electrically connected to one or more of the at least one electrode.

16. The extra cardiac implantable cardioverter defibrillator system of claim 15, wherein the fixation mechanism is a passive fixation mechanism.

17. The extra cardiac implantable cardioverter defibrillator system of claim 10, wherein the dipole is configured to sense and/or pace the right ventricle.

18. The extra cardiac implantable cardioverter defibrillator system of claim 10, further comprising a leadless pacing device configured to be implanted in a chamber of a heart for pacing the heart.

19. The extra cardiac implantable cardioverter defibrillator system of claim 10, further comprising a lead extension coupled to the distal end of the defibrillation lead, the lead extension configured to extend further into the inferior vena cava in the distal direction.

20. The extra cardiac implantable cardioverter defibrillator system of claim 19, wherein the defibrillation lead is configured to float freely in the inferior vena cava.

* * * * *